US007089816B2

(12) United States Patent
Hakimuddin

(10) Patent No.: US 7,089,816 B2
(45) Date of Patent: Aug. 15, 2006

(54) METHOD AND APPARATUS FOR TESTING CEMENT SLURRIES

(75) Inventor: Mustafa Hakimuddin, Katy, TX (US)

(73) Assignee: Halliburton Energy Services, Inc., Duncan, OK (US)

( * ) Notice: Subject to any disclaimer, the term of this patent is extended or adjusted under 35 U.S.C. 154(b) by 170 days.

(21) Appl. No.: 10/756,558

(22) Filed: Jan. 13, 2004

(65) Prior Publication Data

US 2005/0152432 A1 Jul. 14, 2005

(51) Int. Cl.
*G01N 33/38* (2006.01)
(52) U.S. Cl. .................................. 73/866; 73/865.6
(58) Field of Classification Search ............... None
See application file for complete search history.

(56) References Cited

U.S. PATENT DOCUMENTS

| 4,138,892 A |   | 2/1979  | Davis ........................ 73/432  |
|-------------|---|---------|---------------------------------------|
| 4,259,868 A |   | 4/1981  | Rao et al. .................. 73/597  |
| 4,377,087 A | * | 3/1983  | Rodot ........................ 73/594  |
| 5,571,951 A | * | 11/1996 | Jamth ...................... 73/54.03  |
| 6,053,245 A |   | 4/2000  | Haberman                              |
| 2003/0033893 A1 | * | 2/2003 | Go Boncan et al. ....... 73/865.5 |

FOREIGN PATENT DOCUMENTS

| GB | 2 257 256 A | 1/1993 |
| JP | 2000193572  | 7/2000 |

OTHER PUBLICATIONS

Foreign communication from related counterpart application dated Jun. 30, 2005.

* cited by examiner

*Primary Examiner*—Hezron Williams
*Assistant Examiner*—Paul M. West
(74) *Attorney, Agent, or Firm*—John W. Wustenberg; Conley Rose

(57) ABSTRACT

A method and apparatus for testing cement comprising introducing cement into a curing vessel that is at least partially inside a test vessel, curing the cement at a selected temperature and pressure, maintaining the cement at least at the selected temperature and pressure after the cement has cured and until testing of the cement, and testing the cement for a performance property. The testing apparatus comprises a test vessel comprising a test chamber, a curing vessel at least partially within the test chamber comprising a first end cap, a second end cap, and a flexible sleeve, the curing vessel being sealed from the fluid in the test chamber.

67 Claims, 2 Drawing Sheets

METHOD AND APPARATUS FOR TESTING CEMENT SLURRIES

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND

There are various types of wells, such as land based wells and offshore wells, for producing oil, gas, water, or hydrates. Offshore wells may also be shallow or deep water wells. A shallow offshore well is typically drilled from a platform that is in water up to 3,000 feet in depth. A deep water well is drilled from a floating platform or vessel with a riser extending from the sea floor to the platform or submersible rig. Any water deeper than 5,000 feet requires a drilling vessel, typically a drill ship.

Well construction, such as the drilling of an oil or gas well, includes a wellbore or borehole being drilled through a series of formations. Each formation through which the well passes must be sealed to avoid an undesirable passage of formation fluids, gases, or materials out of the formation and into the borehole or from the borehole into the formation. It is also commonly desired to isolate both producing and non-producing formations from each other to avoid contaminating one formation with the fluids from another formation.

To seal or isolate the formations, conventional well architecture includes casing the borehole. The formations may also be cased for borehole stability due to the geo-mechanics of the formation such as compaction forces, seismic forces, and tectonic forces. The casings prevent the collapse of the borehole wall and prevent the undesired outflow of drilling fluids into the formation or the inflow of fluids from the formation into the borehole. The borehole also may need to be cased due to equivalent circulating density and hydraulics reaching or exceeding the formation pore pressure or exceeding the fracture gradient pressure, which would allow fluids or gases to transfer between formations and borehole. If the formations are non-producing, or not of the desired producing interval (some intervals are producing but at low levels), the formations can be cased together. If shallow water flows (where water flows several hundred feet below the seabed floor), or if there is potential communication among formations, then the formation is cased. The casings extend downhole and are sequentially placed across the formations through which the wellbore or borehole passes. The casings may also be liners, which do not extend to the surface of the wellbore. Steel casing can be used to case off formations.

Each succeeding casing placed in the wellbore has an outside diameter reduced in size when compared to the casing previously installed, particularly to accommodate hangers for the inner strings. Thus, a well may be described as a series of nested casing strings. The borehole is drilled in intervals whereby a casing, which is to be installed in a lower borehole interval, is lowered through a previously installed casing of an upper borehole interval. As a consequence of this procedure, the casing of the lower interval has a smaller diameter than the casing of the upper interval. Thus, the casings are in a nested arrangement with casing diameters decreasing in the downward direction. The number of casings required to reach a given target depth is determined principally by the properties of the formations penetrated and by the pressures of the fluids contained in the formations.

Various types of casing may be installed in the well including structural or conductor casing, surface casing, intermediate or production casing, and production liners. Typically, a land based well starts with a 20"/18⅝" or larger diameter casing and telescopes down through two or three intermediate casings, to a final casing size of typically 6⅜" with a 5" production liner installed. Each casing is secured in place with cement filling an annulus having a size typically varying from 1 to 10 inches over the length of the casing and may be as much as 14 to 21 inches or greater at a wash out in the borehole wall.

FIG. 1 is a schematic of a deep water well completion. The size and number of casing and tubing strings will increase or decrease depending upon the well plan based upon, for example, the depth of the well, the production tubing delivery size, the structural support and the seabed formation support. If the seabed formation is unconsolidated and has little support, then the structural or conductor casing is larger and is set deeper. If the initial conductor casing is in rock, then it can be smaller with substantially less depth. For example, initially a structural or conductor casing and riser are lowered from a drilling platform and driven, drilled or jetted into the sea floor to provide support for a surface casing. The structural or conductor casing may or may not be cemented.

FIG. 1 illustrates a 36 inch by 16 inch by 10¾ inch by 7 inch casing program with the addition of one or more tubing strings. After the 36 inch conductor casing is set, one or more surface casings is installed. A borehole is drilled for a 20 inch surface casing which is lowered into place with a 21" surface casing riser attached thereto. A subsea wellhead with blowout prevention equipment, such as an 18¾ inch blowout preventer, is installed on the surface casing. The subsea wellhead may be supported by a structural casing.

Further, a borehole may be drilled through the riser and wellhead and through a problematic formation to extend a structural casing through the problem formation. For example, there are salt formations in the deepwater of the Gulf of Mexico. The structural casing forms a barrier across the formation while also supporting the wellhead. The structural casing has a thicker wall and provides a stable support frame for and can carry the load on the subsea wellhead. A 16 inch structural casing may be drilled, installed and cemented through a salt formation to seal off the salt formation from the wellbore being drilled. It should be appreciated that if there is no problematic formation, such as a salt zone, a shallow water flow zone, loss circulation zone, or other problem zone, then a structural casing is not needed to seal off the problematic area but it will support the subsea or platform wellhead, depending on well type.

Another borehole is then drilled for a 13⅜ inch intermediate casing string which is lowered into the borehole, attached to another riser, and cemented in place. Next a borehole may be drilled for another intermediate casing, such as a 11⅞ inch casing, and cemented in place. The borehole for the production casing string, such as a 9⅝ inch casing, is drilled and the production string is landed. It may or may not be cemented in place. The drilling is performed through blowout prevention equipment.

During the drilling of the wellbore, annuli are provided between the outer surfaces of the casings and the borehole wall and a composition, sometimes referred to as "oil field" cement, is introduced in the annulus for cementing the casing within the wellbore after the installation of each casing. When the casing is located in its desired position in the well, a cement slurry is pumped via the interior of the casing and around the lower end of the casing and upwards into the annulus, thereby causing the cement slurry to drive the drilling fluid upward in the annulus. As soon as the annulus around the casing is sufficiently filled with the cement slurry, injection of cement into the well is stopped and the cement slurry is allowed to harden, or cure. The cement sets up in the annulus, supporting and positioning the casing and forming a substantially impermeable that which divides the well bore into subterranean zones.

Ultimately the borehole reaches the target and is drilled through a hydrocarbon-containing formation or reservoir to produce hydrocarbons. The borehole may or may not be cased through the hydrocarbon-containing reservoir to allow substantially unrestricted influx of fluids from the formation into the borehole.

The purpose of the cement body around the casing is to fix the casing in the well. The cement also seals the borehole around the casing to prevent vertical flow of fluid alongside the casing towards other formation layers or even to the earth's surface. The cement prevents fluid exchange between or among formation layers through which the wellbore passes, and prevents the undesirable migration of fluids between zones or gas from rising up the wellbore.

It is important that there is no gas or fluid leakage after the cement has set and the well is completed. Thus, casing is cemented in place for two main reasons: (1) to seal off and prevent leak paths between permeable zones and/or surface; and (2) to give support and stability to the casings. A problem encountered during cementation of the casing is that due to various factors, such as the existence of varying pressure and temperature gradients along the length of the casing and shrinkage of the cement body during hardening thereof, relative displacements occur between the casing and the hardened cement that may result in poor bonding or cracking between the cement body and the casing.

Poor bonding may result in the presence of a so-called micro-annuli between the casing and cement body that may extend along a substantial part of the length of the casing. The occurrence of a micro-annuli is particularly dangerous in gas wells as substantial amounts of gas might escape to the surface. In some cases, hydrogen sulfide or natural gas can escape into the atmosphere. This condition may also lead to surface or ground water contamination. The resulting problems are very expensive to correct.

The poor bonding of the cement may be attributed to drilling fluid contamination or to bonding of the cement to the casing after the cement has set and/or oil or mill finish contamination on the surface of the casing. Poor bonding may also be contributed to aggressive drilling or aggressive pressure subjection and large pressure differentials prior to it hardening and during the operation. Also, hardening of cement generally causes a slight change of the volume of the cement.

A more fundamental cause of poor bonding is the loss of the hydrostatic head during the curing of the cement such that the formation pressure exceeds the annulus pressure and gas migration occurs causing channeling of the cement and subsequent leakage. For example, during cementing operations, it is common to both reciprocate and rotate the casing during the cement pumping operation to break up or close any cement channels around the casing. Also, compressible cement slurries have additives that entrain gas. During the cement pumping operation, the additives are compressed. As the hydrostatic head is lost during curing of the cement, the entrained gas subsequently expands and prevents loss of the pore pressure such that formation gas is prevented from migrating into the annulus. These specialized cement additives are expensive, however, and require specific operational techniques. This technique may also result in a lower strength cement. Additionally, too much of a hydrostatic head can be detrimental because the cement will take longer to cure and will be soft.

Additionally, heat of hydration, or the amount of heat formed by the curing of the cement, is an important design factor. If curing the cement produces too much heat, the physical characteristics of the casing and the formation can be affected. The properties of the cement itself may also be affected if the curing temperatures become too elevated.

Also, some cement slurries depend on the cement achieving high gel strengths in very short time periods. If there is a rapid static gel strength obtained, gas migration and channeling are reduced or prevented. The strength and capability of the cement to seal against fluid migration between various zones along the production casing is also an important design consideration.

Thus, it is essential that the cement slurry be designed to create a good bond between the cement body and both the casing and the borehole wall in the particular well environment. The various techniques and cement design factors must all be taken into account to form a proper bond between the casing and the formation. The cement must perform in the short term as well as long term through the life of the well. The cement formulation used for cementing wells will thus depend on the mechanical properties of the cement.

BRIEF DESCRIPTION OF THE DRAWINGS

For a more detailed description of the embodiments, reference will now be made to the following accompanying drawings.

DETAILED DESCRIPTION OF THE EMBODIMENTS

The present invention includes embodiments of different forms. The drawings and the description below disclose specific embodiments with the understanding that the embodiments are to be considered an exemplification of the principles of the invention, and are not intended to limit the invention to that illustrated and described. Thus, there can also be different embodiments not described that are still within the principles of the invention. Further, it is to be fully recognized that the different teachings of the embodiments discussed below may be employed separately or in any suitable combination to produce desired results.

Figure 1:
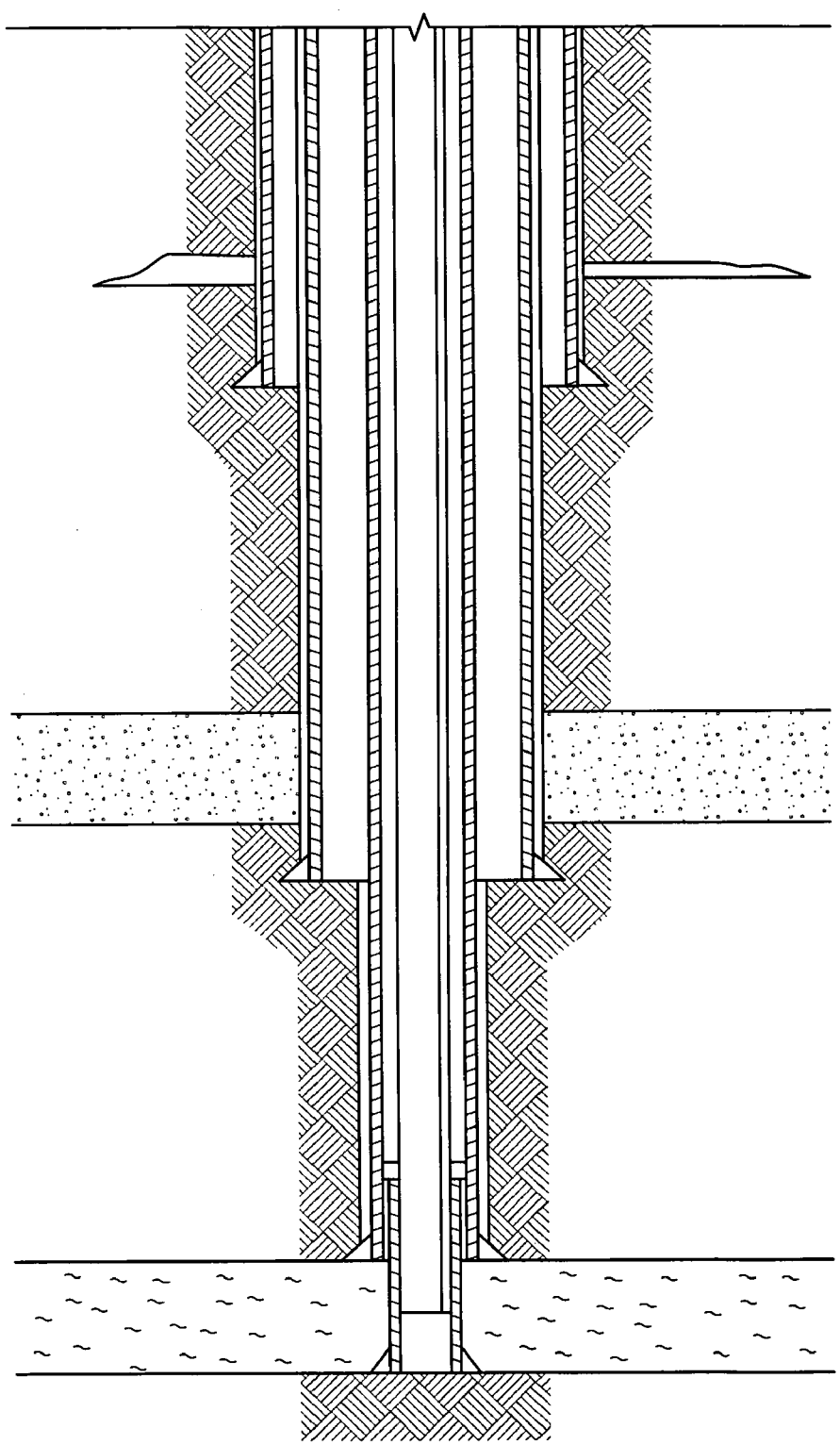
FIG. 1 is a schematic view of a well structure.
Figure 2:
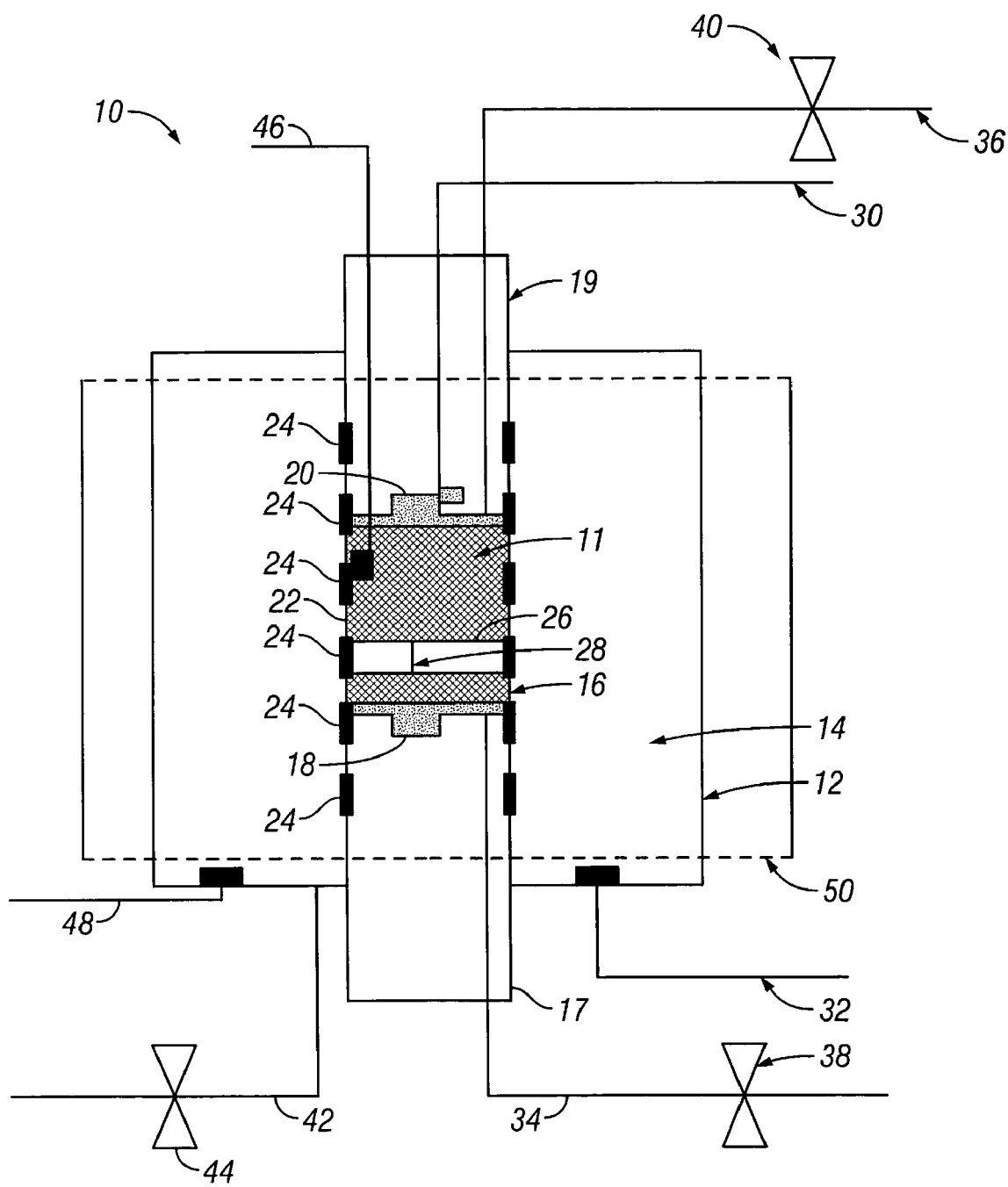
FIG. 2 is a schematic view of the cement testing apparatus.

FIG. 2 shows an embodiment of the cement testing apparatus 10 for testing cement 11. The cement testing apparatus 10 comprises a test vessel 12 comprising a chamber 14 filled with a test vessel fluid. The test vessel fluid can be oil, or any other suitable electrically non-conductive fluid. The testing apparatus 10 further comprises a test vessel inlet flow line 42 controlled by valve 44 for the flow of the test vessel fluid into the chamber 14. The test vessel inlet flow line 42 and valve 44 are adapted to adjust the pressure within the test chamber 14. The test vessel 12 can be made out of any suitable material, such as steel. The test vessel 12 is generally cylindrical in shape but can be any suitable size, shape, or dimension.

Located at least partially inside the chamber 14 of the test vessel 12 is a curing vessel 16. The curing vessel 16 comprises a first end cap 18, a second end cap 20, and a sleeve 22. The sleeve 22 is flexible and can be made of any suitable material, such as Viton or any other type of rubber. The curing vessel 16 can be located completely within the test vessel 12, or only partially within the test vessel 12. The inside of the curing vessel 16 is sealed from the test fluid in the test chamber 14 of the test vessel 12. The first and second end caps 18, 20 are adapted to selectively adjust the volume of the curing vessel 16. The end caps can be adjusted using mechanical, hydraulic, or any other suitable means. The testing apparatus 10 also comprises a curing vessel inlet line 34 and a curing vessel outlet line 36. A valve 38 controls flow through the curing vessel inlet line 34 and a valve 40 controls flow through the curing vessel outlet line 36. The curing vessel inlet line 34 is in fluid communication with the first end cap 18 and the curing vessel outlet line 36 is in fluid communication with the second end cap 20. The lines 34, 36 and valves 38, 40 are used to control flow through the curing vessel 16 as well as to control the pressure inside the curing vessel 16. The flow lines 34, 36 may also be configured in any other suitable manner. If inside the test vessel 12, the curing vessel is secured using curing vessel holders 17, 19, or is secured by any other suitable means.

The testing apparatus 10 further comprises a radial deformation gauge 24 comprising a radial deformation measurement band 26 located around the flexible sleeve 22. The radial deformation gauge 24 also comprises a spring-loaded strain gauge 28 adapted to measure expansion and contraction of the radial deformation band 26 corresponding to the radial expansion and contraction of the sleeve 22. The testing apparatus 10 may also have more than one radial deformation gauge 24. In addition to the radial deformation gauge 24, the end caps 18 and 20 comprise strain gauges (not shown) for measuring the axial expansion and contraction of the cement 11. The axial strain gauges measure the axial expansion and contraction of the cement 11 by measuring the axial movement of at least one of the end caps 18 and 20.

The testing apparatus 10 also comprises a first temperature measurement device 30 adapted to measure the temperature of the cement 11. The testing apparatus 10 also comprises a second temperature measurement device 32 adapted to measure the temperature inside the test chamber 14. The temperature measurement devices 30, 32 may be thermocouples or any other suitable temperature measurement devices are used in conjunction with the necessary equipment for taking the temperature measurements.

The testing apparatus 10 also comprises a first pressure measurement device 46 adapted to measure the pressure inside the curing vessel 16. The testing apparatus further comprises a second pressure measurement device 48 adapted to measure the pressure inside the chamber 14 of the test vessel 12. The pressure measurement devices 46, 48 may be Heise gauges, or any other suitable pressure measurement devices. The pressure measurement devices 46, 48 are also used in conjunction with the necessary equipment for taking the pressure measurements.

The testing apparatus 10 also comprises a heating jacket 50 for adjusting the temperature within the chamber 14 of the test vessel 12. The heating jacket can be located around the test vessel 12, or in any other configuration suitable for controlling the temperature of the temperature within the chamber 14. Any other suitable heating device may also be used.

A first embodiment of the method of testing cement comprises having the curing vessel 16 filled with a curing vessel fluid, such as water or any other suitable fluid. The curing vessel fluid, as well as the test vessel fluid, is at a selected temperature and pressure, such as a temperature and pressure simulating a high temperature, high pressure downhole drilling environment. For example, the curing vessel fluid and test vessel fluid may be at 250° F. and 5000 psi. The pressure inside the curing vessel 16 is such that there is substantially no pressure differential between the inside and the outside of the curing vessel 16. The pressure regulators, such as fluid pumps, and the heating jacket 50 control the pressure and temperature inside the test vessel 12 and the curing vessel 16.

Cement 11 is then introduced into the curing vessel 16 through inlet line 34 and the first end cap 18. As the cement is introduced, the cement 11 displaces the curing vessel fluid from the curing vessel 16 through the second end cap 20 and the outlet line 36. The pressure inside the curing vessel 16 is maintained such that there is substantially no pressure differential between the inside and the outside of the curing vessel 16 as the cement 11 is introduced. The material being displaced from the curing vessel 16 is compared with the cement 11 going into the curing vessel to verify that no curing vessel fluid remains in the curing vessel 16. The comparison may be a made by comparing the densities of the cement in the inlet line 34 with the material in the outlet line 36 or by any other suitable material identifying method. The cement 11 is sealed inside the curing vessel 16 from the test vessel fluid inside the test chamber 14. An appropriate amount of curing vessel fluid head is then placed on top of the cement 11. The amount of curing vessel fluid head will be dependent on the desired testing parameters and may be varied by design.

After the cement 11 is in the curing vessel 16, the cement 11 is allowed to cure at the selected temperature and pressure. During curing, the pressure differential between the inside and the outside of the curing vessel 16 is no longer maintained to be substantially zero. Instead, the pressure differential is allowed to freely adjust as the cement 11 cures. As the cement 11 cures, any change in volume of the cement 11 is monitored using the deformation gauge 24 and the strain gauges for the end caps 18 and 20. A change in volume produces a radial expansion or contraction of the sleeve 22, which moves the radial deformation band 26. The movement of the radial deformation band is then measured by the spring-loaded strain gauge 28. A change in volume also produces an axial expansion or contraction of the cement 11 and thus at least one of the end caps 18 and 20. The strain gauges for the end caps 18 and 20 measure the movement of at least one of the end caps 18 and 20. Thus, any change in volume of the cement 11 during curing is measured. Also monitored is the water of hydration and the heat of hydration during the curing process.

After the cement 11 cures, the cement 11 is maintained at the selected temperature and pressure until the testing of the cement 11 commences. The pressure and temperature of the cement 11 are never allowed to drop below the selected levels until the testing commences. During testing, the pressure and temperature fluctuate depending on the nature and parameters of the tests performed. The tests performed can be of any suitable type to measure any desired performance property of the cement 11. The tests can include hydrostatic, unconfined, confine, uni-axial, hydrostatic cycling, confine axial, shear bonding, and pore pressure cycling tests. The tests can measure parameters such as axial pressure, radial pressure, pore pressure, axial strain, circumferential strain, longitudinal acoustic velocity, shear acoustic velocity, water of hydration, heat of hydration, and permeability of the cement 11. The performance properties measured can include Young's Modulus, Poisson's Ratio, Fatigue, Failure Strength, Dynamic Young's Modulus, and Dynamic Poisson's Ratio. The tests and properties described are known in the art and are not meant to be an exhaustive list of all the tests that may be performed.

The tests may also be performed in any suitable manner. For example, the volume of the curing vessel may be adjusted. This may be done by any suitable means, including moving at least one of the end caps 18, 20. The end caps 18, 20 may be moved by any suitable means, such as mechanically or hydraulically.

A second embodiment of the method of testing cement comprises having the inside of the curing vessel 16 at ambient temperature and pressure, the curing vessel filled only with ambient gasses, before the cement 11 is introduced. The chamber 14 of the test vessel 12 is filled with test vessel fluid also at ambient temperature and pressure.

The cement 11 is then introduced into the curing vessel 16 through inlet line 34 and the first end cap 18. The test vessel 12 is then brought to the selected temperature and pressure, such as a temperature and pressure simulating a high temperature, high pressure downhole drilling environment. For example, the test vessel 12 may be brought to 250° F. and 5000 psi. While adjusting the temperature and pressure of the test vessel 12, the pressure inside the curing vessel 16 is also maintained such that there is substantially no pressure differential between the inside and the outside of the curing vessel 16. An appropriate amount of curing vessel fluid head is also added to the top of the cement 11. The amount of curing vessel fluid head will be dependent on the desired testing parameters and may be varied by design.

Once at the selected temperature and pressure, the cement 11 is allowed to cure at the selected temperature and pressure. The cement 11 is also maintained at the selected temperature and pressure until commencing the testing of the cement 11. During the curing and until the testing, the cement 11 is maintained above the selected temperature and pressure. Once the cement 11 cures, the method of testing the cement 11 proceeds as described as in the first embodiment While specific embodiments have been shown and described, modifications can be made by one skilled in the art without departing from the spirit or teaching of this invention. The embodiments as described are exemplary only and are not limiting. Many variations and modifications are possible and are within the scope of the invention. Accordingly, the scope of protection is not limited to the embodiments described, but is only limited by the claims that follow, the scope of which shall include all equivalents of the subject matter of the claims.

What is claimed is:

1. A method of testing cement comprising:
   introducing cement into a curing vessel that is at least partially inside a test vessel, the curing vessel comprising a flexible sleeve;
   adjusting the cement temperature and pressure to a selected temperature and pressure while maintaining substantially no pressure differential between the inside and the outside of the flexible sleeve;
   curing the cement at the selected temperature and pressure;
   maintaining the cement at least at the selected temperature and pressure after the cement has cured and until testing of the cement;
   testing the cement for a performance property; and
   the curing vessel being filled with a curing vessel fluid and the test vessel being filled with a test vessel fluid before introducing the cement into the curing vessel such that there is substantially no pressure differential between the inside and the outside of the flexible sleeve.

2. The method of claim 1 further comprising:
   displacing a curing vessel fluid from the curing vessel when introducing the cement into the curing vessel, the test vessel being at the selected temperature and pressure; and
   maintaining substantially no pressure differential between the inside and outside of the flexible sleeve as the cement is introduced into the curing vessel.

3. The method of claim 2 further comprising:
   comparing the cement going into the curing chamber with the material being displaced out of the curing vessel to verify that no curing vessel fluid remains in the curing chamber; and
   placing a selected curing vessel fluid head on the cement.

4. The method of claim 1 further comprising introducing the cement through a first fluid line controlled by a first valve, the curing vessel further comprising first and second end caps engageable with the flexible sleeve to contain the cement within the curing vessel.

5. The method of claim 1 further comprising allowing the pressure differential between the inside and the outside of the flexible sleeve to adjust as the cement cures.

6. The method of claim 1 further comprising maintaining the pressure in the test vessel above 5000 pounds per square inch while the cement cures.

7. The method of claim 1 further comprising maintaining the pressure in the test vessel with a pressure regulator.

8. The method of claim 1 further comprising maintaining the temperature in the test vessel above 250° F. while the cement cures.

9. The method of claim 1 further comprising maintaining the temperature in the test vessel with a heating jacket around the test vessel.

10. The method of claim 1 further comprising measuring the change in volume of the cement in the curing vessel during curing.

11. The method of claim 10 further comprising measuring the change of the cement in the radial dimension with a first strain gauge and measuring the change of the cement in the axial dimension with a second strain gauge.

12. The method of claim 11 further comprising:
    the curing vessel further comprising first and second end caps engageable with the flexible sleeve to contain the cement within the curing vessel; and
    the first strain gauge measuring the change of the flexible sleeve in the radial dimension and the second strain gauge measuring the change of at least one of the first and second end caps in the axial dimension.

13. The method of claim 1 where the testing of the cement comprises a test selected from the group consisting of hydrostatic, unconfined, confine, uni-axial, hydrostatic cycling, confine axial, shear bonding, and pore pressure cycling.

14. The method of claim 1 where the testing of the cement comprises a test measuring a parameter selected from the group consisting of axial pressure, radial pressure, pore pressure, axial strain, circumferential strain, longitudinal acoustic velocity, shear acoustic velocity, water of hydration, heat of hydration, and permeability.

15. The method of claim 1 where the performance property is selected from the group consisting of Young's Modulus, Poisson's Ratio, Fatigue, Failure Strength, Dynamic Young's Modulus, and Dynamic Poisson's Ratio.

16. The method of claim 1 further comprising testing the cement by adjusting the pressure inside the curing vessel with a pressure fluid inlet line.

17. The method of claim 1 further comprising testing the cement by adjusting the volume of the curing vessel.

18. The method of claim 17 further comprising adjusting the volume of the curing vessel by moving at least one of a first and second curing vessel end cap.

19. The method of claim 1 where the flexible sleeve is rubber.

20. The method of claim 1 where the flexible sleeve is a fluoroelastomer.

21. A method of testing cement comprising:
  introducing a curing vessel fluid into a curing vessel that is at least partially inside a test vessel, the curing vessel comprising a flexible sleeve;
  adjusting the curing vessel fluid temperature and pressure to a selected temperature and pressure while maintaining substantially no pressure differential between the inside and the outside of the flexible sleeve;
  displacing a curing vessel fluid from within the curing vessel by introducing cement into the curing vessel while maintaining substantially no pressure differential between the inside and the outside of the flexible sleeve as the cement is introduced into the curing vessel;
  curing the cement at the selected temperature and pressure;
  maintaining the cement at least at the selected temperature and pressure after the cement has cured and until testing of the cement; and
  testing the cement for a performance property.

22. The method of claim 21 further comprising the test vessel being filled with a test vessel fluid.

23. The method of claim 21 further comprising:
  comparing the cement going into the curing vessel with the material being displaced out of the curing vessel to verify that no curing vessel fluid remains in the curing vessel; and
  placing a selected curing vessel fluid head on the cement.

24. The method of claim 21 further comprising introducing the cement through a first fluid line controlled by a first valve, the curing vessel further comprising first and second end caps engageable with the flexible sleeve to contain the cement within the curing vessel.

25. The method of claim 21 further comprising allowing the pressure differential between the inside and the outside of the flexible sleeve to adjust as the cement cures.

26. The method of claim 21 further comprising maintaining the pressure in the test vessel above 5000 pounds per square inch while the cement cures.

27. The method of claim 21 further comprising maintaining the pressure in the test vessel with a pressure regulator.

28. The method of claim 21 further comprising maintaining the temperature in the test vessel above 250° F. while the cement cures.

29. The method of claim 21 further comprising maintaining the temperature in the test vessel with a heating jacket around the test vessel.

30. The method of claim 21 further comprising measuring the change in volume of the cement in the curing vessel during curing.

31. The method of claim 30 further comprising measuring the change of the cement in the radial dimension with a first strain gauge and measuring the change of the cement in the axial dimension with a second strain gauge.

32. The method of claim 31 further comprising:
  the curing vessel further comprising first and second end caps engageable with the flexible sleeve to contain the cement within the curing vessel; and
  the first strain gauge measuring the change of the flexible sleeve in the radial dimension and the second strain gauge measuring the change of at least one of the first and second end caps in the axial dimension.

33. The method of claim 21 where the testing of the cement comprises a test selected from the group consisting of hydrostatic, unconfined, confine, uni-axial, hydrostatic cycling, confine axial, shear bonding, and pore pressure cycling.

34. The method of claim 21 where the testing of the cement comprises a test measuring a parameter selected from the group consisting of axial pressure, radial pressure, pore pressure, axial strain, circumferential strain, longitudinal acoustic velocity, shear acoustic velocity, water of hydration, heat of hydration, and permeability.

35. The method of claim 21 where the performance property is selected from the group consisting of Young's Modulus, Poisson's Ratio, Fatigue, Failure Strength, Dynamic Young's Modulus, and Dynamic Poisson's Ratio.

36. The method of claim 21 further comprising testing the cement by adjusting the volume of the curing chamber.

37. The method of claim 36 further comprising adjusting the volume of the curing chamber by moving at least one of a first and second curing vessel end caps.

38. The method of claim 21 wherein the curing vessel further comprises first and second end caps engageable with the flexible sleeve to contain the cement within the curing vessel.

39. The method of claim 21 where the flexible sleeve is rubber.

40. The method of claim 21 where the flexible sleeve is a fluoroelastomer.

41. A method of testing cement comprising:
  introducing cement into a curing vessel at least partially inside a test vessel, the curing vessel comprising a flexible sleeve and first and second end caps engageable with the flexible sleeve to contain the cement within the curing vessel;
  placing a selected curing vessel fluid head on the cement;
  adjusting the temperature and pressure of the test vessel to a selected temperature and pressure while maintaining substantially no pressure differential between the inside and the outside of the flexible sleeve until the test vessel reaches the selected temperature and pressure;
  curing the cement at the selected temperature and pressure;
  measuring the change in volume of the cement in the curing vessel during curing, comprising:
    measuring the change of the cement in the radial dimension with a first strain gauge that measures the change of the flexible sleeve in the radial dimension; and
    measuring the change of the cement in the axial dimension with a second strain gauge that measures the change of at least one of the first and second end caps in the axial dimension;

maintaining the cement at least at the selected temperature and pressure after the cement has cured and until testing of the cement; and testing the cement for a performance property.

42. The method of claim 41 further comprising introducing the cement through a first fluid line controlled by a first valve.

43. The method of claim 41 further comprising allowing the pressure differential between the inside and the outside of the flexible sleeve to adjust as the cement cures.

44. The method of claim 41 further comprising maintaining the pressure in the test vessel above 5000 pounds per square inch while the cement cures.

45. The method of claim 41 further comprising maintaining the pressure in the test vessel with a pressure regulator.

46. The method of claim 41 further comprising maintaining the temperature in the test vessel above 250° F. while the cement cures.

47. The method of claim 41 further comprising maintaining the temperature in the test vessel with a heating jacket around the test vessel.

48. The method of claim 41 where the testing of the cement comprises a test selected from the group consisting of hydrostatic, unconfined, confine, uni-axial, hydrostatic cycling, confine axial, shear bonding, and pore pressure cycling.

49. The method of claim 41 where the testing of the cement comprises a test measuring a parameter selected from the group consisting of axial pressure, radial pressure, pore pressure, axial strain, circumferential strain, longitudinal acoustic velocity, shear acoustic velocity, water of hydration, heat of hydration, and permeability.

50. The method of claim 41 where the performance property is selected from the group consisting of Young's Modulus, Poisson's Ratio, Fatigue, Failure Strength, Dynamic Young's Modulus, and Dynamic Poisson's Ratio.

51. The method of claim 41 further comprising testing the cement by adjusting the volume of the curing chamber.

52. The method of claim 51 further comprising adjusting the volume of the curing chamber by moving at least one of the first and second end caps.

53. The method of claim 41 where the flexible sleeve is rubber.

54. The method of claim 41 where the flexible sleeve is a fluoroelastomer.

55. The method of claim 41 further comprising testing the cement by adjusting the pressure inside the curing vessel with a pressure fluid inlet line.

56. A testing apparatus for testing cement comprising:
a test vessel comprising a fluid-filled test chamber;
a curing vessel at least partially within the test chamber comprising a first end cap, a second end cap, and a flexible sleeve, the curing vessel being sealed from the fluid in the test chamber; and
the first and second end caps adapted to selectively adjust the volume of the curing vessel.

57. The testing apparatus of claim 56 further comprising a radial deformation gauge comprising a radial deformation measurement band around the flexible sleeve and a spring-loaded strain gauge adapted to measure change of the radial deformation band in the radial dimension corresponding to the change in the radial dimension of the flexible sleeve.

58. The testing apparatus of claim 56 where the flexible sleeve is rubber.

59. The testing apparatus of claim 58 where the flexible sleeve is a fluoroelastomer.

60. The testing apparatus of claim 58 further comprising a first temperature measurement device adapted to measure the temperature of the cement and a second temperature measurement device adapted to measure the temperature of the test chamber.

61. The testing apparatus of claim 56 further comprising a curing vessel inlet line and a curing vessel outlet line adapted to adjust the pressure within the curing vessel.

62. The testing apparatus of claim 61 wherein the curing vessel inlet line is in fluid communication with the first end cap and the curing vessel outlet line is in fluid communication with the second end cap.

63. The testing apparatus of claim 62 further comprising a first valve to control flow through the curing vessel inlet line and a second valve to control flow through the curing vessel outlet line.

64. The testing apparatus of claim 56 further comprising a test vessel inlet line adapted to adjust the pressure within the test chamber.

65. The testing apparatus of claim 56 further comprising a first pressure measurement device adapted to measure the pressure inside the curing vessel and a second pressure measurement device adapted to measure the pressure inside the test vessel.

66. The testing apparatus of claim 56 further comprising a heating jacket for adjusting the temperature within the test chamber.

67. The testing apparatus of claim 56 further comprising an axial deformation gauge comprising a axial strain gauge adapted to measure the axial movement of at least one of the first and second end caps.

* * * * *